US00PP18991P2

(12) United States Plant Patent
van Kleinwee et al.

(10) Patent No.: US PP18,991 P2
(45) Date of Patent: Jul. 1, 2008

(54) ***BIDENS FERULIFOLIA* PLANT NAMED 'BIDORI'**

(50) Latin Name: *Bidens ferulifolia*
Varietal Denomination: Bidori

(75) Inventors: Theodorus Cornelis Maria van Kleinwee, Hoorn (NL); Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 51 days.

(21) Appl. No.: 11/639,633

(22) Filed: Dec. 15, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—S. Matthew Edwards

(57) ABSTRACT

A new *Bidens* plant named 'Bidori' particularly distinguished by its trailing plant habit and golden yellow flowers all over the plants.

1 Drawing Sheet

Latin name of the genus and species of the plant claimed: *Bidens ferulifolia.*
Varietal denomination: 'Bidori'.

BACKGROUND OF THE NEW PLANT

The present invention relates to a new distinct cultivar of *Bidens,* botanically known as *Bidens ferulifolia,* native to South USA and Mexico.

The new cultivar is propagated by cuttings resulting from a seedling from a combination between two unnamed selections from own breeding of *Bidens ferulifolia* 'B0539-1' and 'A0320.' Seed of this combination was harvested in 2001 and the new variety 'Bidori' was selected in 2002 as one of the plants of this population. This new plant is an annual.

The new cultivar is a product of a planned breeding program conducted by the inventor in Enkhuizen, The Netherlands. The new *Bidens* is trailing, vigorous, and floriferous. 'Bidori' was asexually reproduced by cuttings over a 4 year period and trialled under different conditions in Europe. The new variety is stable and reproduces true to type in successive generations of asexual reproduction.

DESCRIPTION OF THE DRAWING

This new *Bidens* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Bidens* plant. The data which defines these characteristics were collected from asexual reproductions carried out in Enkhuizen, Netherlands. The plant history was taken on 30 week old plants, grown in the open field in Enkhuizen, The Netherlands with day temperatures ranging from 16–30° Celsius, and night temperatures ranging from 10–16° Celsius.

Color references are primarily to the R.H.S. Colour Chart of The Royal Horticultural Society of London.

TABLE 1

COMPARISON BETWEEN THE NEW CULTIVAR AND TWO SIMILAR CULTIVARS

| | 'Bidcomtis' (U.S. Plant Pat. No. 17,326) | 'Peter's Goldteppich' (U.S. Plant Pat. No. 12,880) | 'Bidori' |
|---|---|---|---|
| Plant height | 32-38 cm | 30-35 cm | 40-45 cm |
| Plant width | up to 80 cm | 110-120 cm | 100-120 cm |
| Seed set | present | present | present |
| Internode length | 2-4 cm | 7-11 cm | 6-10 cm |
| Number of petals | 5 | 5-6 | 5-8 |
| Floriferousness | Continuously throughout summer on whole plant | Not flowering in center of plant, stops flowering at end of Summer | Continuously throughout Summer on whole plant |

The plant:

*Classification.*—Botanical: *Bidens ferulifolia* cv. 'Bidori'.

Parentage:

*Female parent.*—*Bidens ferulifolia* 'B0539-1,' an unpatented selection of own breeding, selected in 2000.

*Male parent.*—*Bidens ferulifolia* 'A0320,' an unpatented selection of own breeding, selected in 1999.

*Breeders code of this new variety.*—'D1033-1'.

Propagation:

*Type cuttings.*—Terminal cuttings.

*Time to initiated roots.*—10–12 days at air temperature of 21° C.

*Time to develop roots.*—14–18 days at air temperature of 17° C.

Plant description:

*Growth habit.*—Trailing.

*Plant height.*—40–45 cm.

*Vigor.*—Much more vigorous than *Bidens ferulifolia* cv. 'Bidcomtis' and comparible to 'Peter's Goldteppich'.

*Spreading area of plant.*—100–120 cm.

*Strength.*—Resistant to hot and cold weather.

*Branching character.*—Freely branching and lateral branching at every node.
*Number of branches per plant.*—8 branches/plant.
*Crop time.*—12 weeks.

The stem:
*Diameter.*—4.5 mm.
*Shape.*—Cylindrical.
*Length of plant stem.*—Up to 60 cm.
*Length of lateral branch.*—Up to 60 cm.
*Anthocyanin pigmentation.*—Present, can get as dark as RHS N199A in old stems.
*Length of internode.*—6–18 cm depending on light conditions.
*Pubescence.*—Occasionally some pubescence near nodes. Pubescence absent on rest of stem.
*Color.*—Young stem: RHS 59A. Older stem : With anthocyan pigmentation, between RHS 144A and RHS N199A.

The foliage:
*Arrangement.*—Opposite, but alternate on flower stems.
*Shape of leaf.*—2-pinnate fern-like leaves.
*Leaf apex.*—Apiculate.
*Leaf base.*—Acute.
*Leaf margin.*—Laciniate.
*Texture.*—Smooth young leaves.
*Leaf length.*—1.5–3.7 cm.
*Leaf width.*—1.7–3.3 cm.
*Depth of incision.*—Fully incised.
*Color.*—Upper side: Young leaf RHS 143A. Old leaf RHS 137A. Lower side: Young leaf RHS 144A. Old leaf RHS 146BC.
*Pubescence.*—Some pubescence near base of petiole, absent on rest of leaf and petiole.
*Petiole.*—Length: 0.7–1.5 cm. Color: RHS 152B. Diameter: 1 mm.
*Venation.*—Shape: Pinnate. Color: RHS 146B, upper and lower surface.

The bud:
*Peduncle.*—Length: 2.5–5.5 cm. Diameter: 1 mm. Angle: 45° at base of peduncle; bending more towards main stem at the end. Strength: Flexible. Color: Varying between RHS 143B and RHS 143C.
*Size of the bud.*—Length: 0.6–0.9 cm. Diameter: 0.5 cm.
*Shape.*—Oblong.
*Color.*—RHS 9A.

The inflorescence:
*Flowering season.*—Continuous and free flowering throughout spring summer and fall.
*Diameter of disc.*—2.5–3.5 cm.
*Depth of disc.*—6 mm.
*Form.*—Capitulum with 1 series of ray florets and more series of disc florets.
*Overlapping of ray florets.*—Separate ray florets, but little overlap in flower head.
*Receptacle.*—Shape: Brush-shape. Height: 2.5 mm. Color: RHS 145A.
*Fragrance.*—Weak.
*Number of flowers per plant.*—±100 flowers per plant depending on growth conditions and age of plant.
*Lastingness of flowers on plant.*—7 days.

Ray florets:
*No. of ray florets per inflorescence.*—5–8.
*Size.*—Length: 1.1–1.7 cm. Width: 0.8–1.0 cm. Shape: Ovate. Apex: Tri-dentate. Base: Obtuse. Margin: Entire. Texture: Smooth.
*Color.*—Upper side: More bright and intense golden yellow than RHS 9A. Lower side: RHS 9A.

Disc florets:
*No. of disc florets per inflorescence.*—±50–60 disc florets/inflorescence.
*Size.*—Length when in flower: 6–7 mm. Width: 1 mm.
*Disc floret.*—Shape: Tubular, elongated. Apex: Five-pointed. Base: Fused. Margin: Entire. Texture: Smooth.
*Color of upper and lower side.*—RHS 14A.

Phyllary:
*Number of phyllaries.*—8–9 green ones (RHS 137A) at the lower part of the receptacle and 6–8 yellow ones (RHS 151A with stripe RHS 152B) near to the ray florets.
*Size.*—Length: 4–6 mm. Width: 1–1.5 mm. Shape: Elongated elliptic. Apex: Acute. Base: Truncate. Margin: Entire. Texture: Very lightly pubescent.

Reproductive organs:
*Androecium.*—Location: Present on disc florets only. Anther color: RHS 200A. Anther size: 1.3 mm long. Stamen number: 5. Pollen color: RHS 17A. Amount of pollen: Few.
*Gynoecium.*—Location: Present on ray and disc florets. Pistil number: 50–60 pistils/inflorescence. Pistil length: 4 mm. Style Length: 2.5 mm. Ovary — Number : One per pistil. Size: 0.2 mm diameter, 2.1 mm long. Ovary color: RHS 149C. Style color: RHS 15A. Stigma shape: Bifurcate. Stigma color: RHS 15A.

Seed:
*Production.*—Yes.
*Size.*—Length: 0.6–0.9 cm, including awns of 1.5 mm. Diameter: 0.4–0.6 mm.
*Color.*—RHS 202A.
*Shape.*—2, occasionally 3 rigid awns with minute reflexed points on the achene.

Disease resistance and tolerance for weather conditions: Good tolerance to heat. No specific susceptibility for pests or diseases has been observed to date.

What is claimed is:

1. A new and distinct variety of *Bidens* plant, substantially as herein illustrated and described.

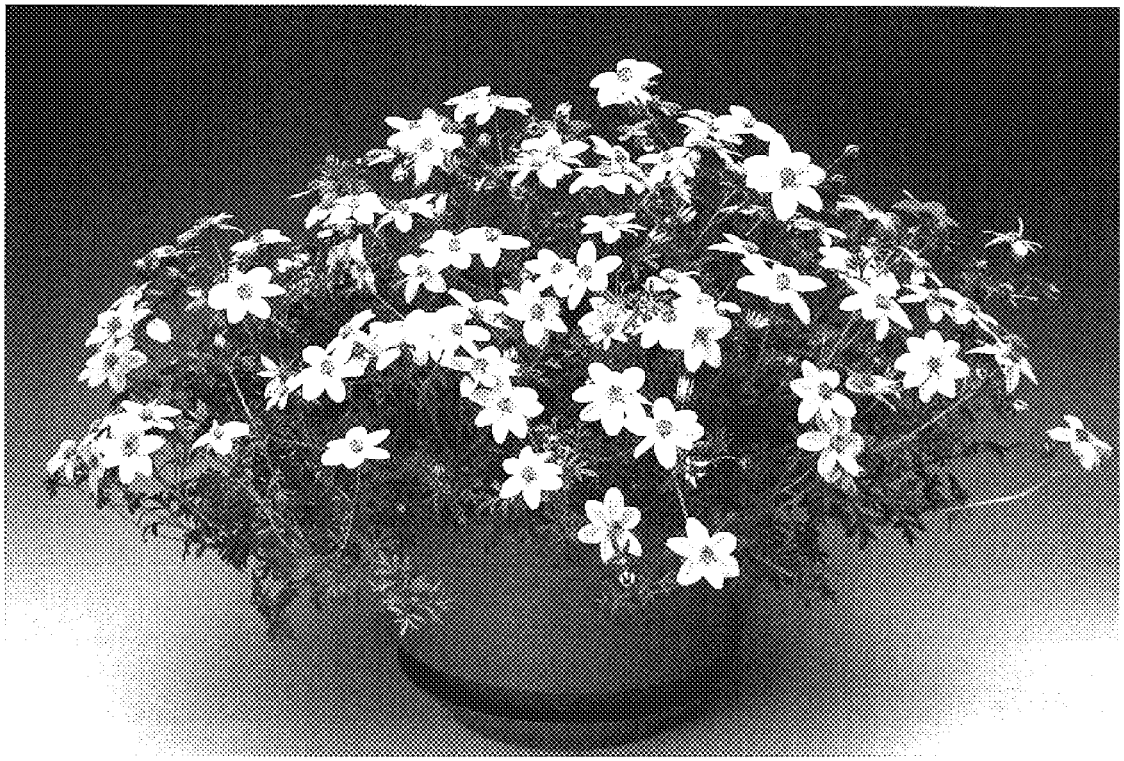

* * * * *